US007514407B2

(12) United States Patent
Averback

(10) Patent No.: US 7,514,407 B2
(45) Date of Patent: Apr. 7, 2009

(54) SPHERON COMPONENT PEPTIDES AND PHARMACEUTICAL COMPOSITIONS

(75) Inventor: Paul Averback, Quebec (CA)

(73) Assignee: Nymox Corporation, St. Laurent, Quebec (CA)

( * ) Notice: Subject to any disclaimer, the term of this patent is extended or adjusted under 35 U.S.C. 154(b) by 453 days.

(21) Appl. No.: 10/444,070

(22) Filed: May 23, 2003

(65) Prior Publication Data

US 2004/0029809 A1    Feb. 12, 2004

Related U.S. Application Data

(63) Continuation-in-part of application No. 10/378,065, filed on Mar. 4, 2003.

(51) Int. Cl.
*A61K 38/10* (2006.01)
*A61K 38/17* (2006.01)
*C07K 7/02* (2006.01)
*C07K 7/08* (2006.01)
*C07K 14/47* (2006.01)

(52) U.S. Cl. ............... 514/14; 514/12; 530/327; 530/324; 530/300

(58) Field of Classification Search ............... None
See application file for complete search history.

(56) References Cited

U.S. PATENT DOCUMENTS

| | | | | |
|---|---|---|---|---|
| 4,587,046 | A | * 5/1986 | Goodman et al. | ........... 530/330 |
| 5,525,339 | A | 6/1996 | Averback | |
| 5,567,720 | A | 10/1996 | Averback | |
| 5,955,285 | A | 9/1999 | Averback | |
| 6,121,036 | A | 9/2000 | Ghanbari et al. | |
| 6,130,221 | A | 10/2000 | Averback et al. | |
| 6,140,467 | A | * 10/2000 | Ware | ........... 530/350 |
| 6,309,892 | B1 | 10/2001 | Averback | |
| 2002/0112251 | A1* | 8/2002 | McCarthy et al. | ........... 800/8 |
| 2005/0191711 | A1* | 9/2005 | Averback | |

FOREIGN PATENT DOCUMENTS

| | | |
|---|---|---|
| GB | 2 352 631 A | 2/2001 |
| WO | WO 98/34643 | 8/1998 |
| WO | WO 98/52898 | 11/1998 |
| WO | WO 99/55839 | 11/1999 |
| WO | WO 03/074558 A2 | 9/2003 |
| WO | 2004/097420 | * 11/2004 |

OTHER PUBLICATIONS

Benkirane 1993. Journal of Biological Chemistry 268:26279-26285.*
Ben-Yedidia et al. 2002. Molecular Immunology 39:323-331.*
Kreitman 1999. Current Opinion in Immunology 11:570-578.*
Zhang 1998. Current Protocols in Molecular Biology 10.15.1-10.15.9*
Mzhavia 2001 Journal of Biological Chemistry 276:6207-6213.*
Sayah 2001 Journal of Neurochemistry 76:1833-1841.*
Fricker et al.; "*Identification and Characterization of proSAAS, a Grain-Like Neuroendocrine Peptide Precursor that Inhibits Prohormone Processing*"; The Journal of Neuroscience, Jan. 15, 2000; 20(2):639-648.
Basak et al.: "*Inhibitory Specificity and Potency of proSAAS-derived Peptides toward Proprotein Convertase 1*" The Journal of Biological Chemistry, vol. 276, No. 35, Aug. 31, 2001.
Cameron et al.: "*Polyarginines Are Potent Furin Inhibitors*" The Journal of Biological Chemistry, vol. 275, No. 47, Nov. 24, 2000.
Fricker et al.: *Identification and Characterization of proSAAS, a Granin-Like Neuroendocrine Peptide Precursor that Inhibits Prohormone Processing*: The Journal of Neuroscience, vol. 20, No. 2, Jan. 15, 2000.
Qian et al.; "*The C-terminal Region of proSAAS Is a Potent Inhibitor of Prohormone Convertase 1*" The Journal of Biological Chemistry, vol. 275, No. 31, Aug. 4, 2000.
International Search Report dated Sep. 4, 2003 issued for PCT/CA03/00295.

* cited by examiner

*Primary Examiner*—Daniel E. Kolker
(74) *Attorney, Agent, or Firm*—Goodwin Procter LLP

(57) ABSTRACT

The present invention relates to racemized proteins and racemized protein components of spherons that are useful for identifying compounds capable of preventing and/or ameliorating symptoms of Alzheimer's Disease and/or dementia associated with cerebral amyloidosis. The invention also relates to the compounds identified by the methods, and methods of treating and/or ameliorating symptoms of Alzheimer's Disease and/or dementia associated with cerebral amyloidosis. The invention also relates to methods of making an Alzheimer's Disease or dementia associated with cerebral amyloidosis animal model or test animal, the animal model produced therefrom, and to a method of using the animal model to screen for effective therapies.

12 Claims, No Drawings

SEQUENCE LISTING

```
<160> NUMBER OF SEQ ID NOS: 29

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Glu Ala Ala Gly Ala Val Gln Glu Leu Ala Arg
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Leu Ser Ala Ala Ser Pro Pro Leu Ala Glu Thr Gly Ala Pro Arg
1               5                   10                  15

<210> SEQ ID NO 3
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 3

Ala Arg Ala Glu Ala Gln Glu Ala Glu Asp Gln Gln Ala Arg
 1               5                  10

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Leu Ala Gln Leu Leu Arg
 1               5

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Leu Ala His Leu Leu Glu Ala Glu Arg Gln Glu Arg
 1               5                  10

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ala Asp His Asp Val Gly Ser Glu Leu Pro Pro Glu Gly Val Leu
 1               5                  10                  15

Gly Ala Leu Leu Arg
             20

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Glu Thr Pro Ala Pro Gln Val Pro Ala Arg
 1               5                  10

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Leu Ala Gly Ser Ala Asp Ser Glu Gly Val Ala Ala Pro Arg
 1               5                  10                  15
```

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Arg Pro Val Lys Glu Pro Arg Gly Leu Ser Ala Ala Ser Pro Pro
 1               5                  10                  15

Leu Ala Glu Thr Gly Ala Pro Arg Arg Phe
             20                  25

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Arg Pro Val Lys Glu Pro
 1               5

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Leu Ser Ala Ala Ser Pro Pro Leu Ala Glu Thr Gly Ala Pro Arg
 1               5                  10                  15

Arg Phe

<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ala Asp His Asp Val Gly Ser Glu Leu Pro Pro Glu Gly Val Leu
 1               5                  10                  15

Gly Ala Leu Leu Arg Val Lys Arg Leu Glu Thr Pro Ala Pro Gln Val
             20                  25                  30

Pro Ala

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ala Asp His Asp Val Gly Ser Glu Leu Pro Pro Glu Gly Val Leu
 1               5                  10                  15

```
Gly Ala Leu Leu Arg Val
            20

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Glu Thr Pro Ala Pro Gln Val Pro Ala
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Arg Ser Val Pro Arg Gly Glu Ala Ala Gly
 1               5                  10

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Leu Ala Gln Leu Leu Arg Val Trp Gly Ala Pro Arg Asn Ser Asp
 1               5                  10                  15

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Ala Leu Gly Leu Asp Asp Asp Pro Asp Ala Pro Ala Ala Gln Leu
 1               5                  10                  15

Ala Arg

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Ala Arg Ala Leu Leu Arg Ala Arg Leu Asp Pro Ala Ala Leu Ala
 1               5                  10                  15

Ala

<210> SEQ ID NO 19
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Leu Val Pro Ala Pro Val Pro Ala Ala Leu Arg Pro Arg Pro
 1               5                  10                  15

Pro Val Tyr Asp Asp
            20

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Pro Ala Gly Pro Asp Ala Glu Glu Ala Gly Asp Glu
 1               5                  10

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Pro Asp Val Asp Pro Glu Leu Leu Arg Tyr Leu Leu Gly Arg
 1               5                  10                  15

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Leu Arg Val Lys Arg
 1               5

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Leu Gly Ala Leu Leu Arg Val Lys Arg Leu Glu
 1               5                  10

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 24

Glu Asn Lys His Gly
 1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Asp Gly Ile Val Thr Asp Ala Ile Glu
 1               5                  10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Trp Gly Pro Asn Asp Asp
 1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Trp Ala Ser Gly Asn Gly
 1               5

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Asp Gly Tyr Thr Asp Ser Ile Tyr Thr Ile
 1               5                  10

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

His Thr Gly Thr Ser
 1               5
```

SPHERON COMPONENT PEPTIDES AND PHARMACEUTICAL COMPOSITIONS

RELATED APPLICATIONS

This application is a continuation-in-part of application entitled: "Spheron Component Useful in Determining Compuonds Capable of Treating Symptoms of Alzheimer's Disease, and Animal Model Produced Thereof," filed on Mar. 4, 2003, application Ser. No. 10/378,065.

BACKGROUND OF THE INVENTION

1. Field of the Invention

The present invention relates to purified protein components of spherons, or racemized protein components of spherons, that are useful for screening compounds capable of preventing and/or ameliorating symptoms associated with cerebral amyloidosis, dementia, or Alzheimer's Disease. The invention also relates to methods of making an Alzheimer's Disease or dementia animal model, the animal model produced therefrom, and to a method of using the animal model to screen for effective Alzheimer's Disease therapies. The invention further relates to methods and compositions that prevent the release of, or reduce the concentration of proSAAS protein or fragments thereof, or block, compete with, or attenuate the effects of increased amounts of proSAAS protein or fragments thereof, in the brain.

2. Description of Related Art

Classified under the rubric "amyloidosis" are a number of pathological conditions characterized by the deposition of abnormal fibrils ("amyloid fibrils") in extracellular spaces. The amyloid fibril, in turn, represents a final common pathway for a diverse array of proteins. Regardless of their biochemical composition, however, all types of amyloid fibrils share (a) a β-pleated sheet structure, (b) green birefringence under polarized light after staining with Congo Red dye, and (c) a fibrillar morphology that has a typical electron-microscopic appearance.

The deposition of amyloid fibrils can affect several organs in the systemic forms of the disorder, exemplified by familial Mediterranean fever, familial amyloid polyneuropathy and systemic amyloidosis, or it can be restricted to one organ in localized forms. Among the latter are conditions classified under the rubric "cerebral amyloidosis," which covers the Alzheimer group of diseases, namely, Alzheimer's disease (pre-senile dementia, senile dementia); Alzheimer's disease associated with Down' syndrome; Alzheimer's disease associated with other central-nervous-system diseases, such as Parkinson's disorder; and congophilic angiopathy (associated or not associated with Alzheimer's disease). Alzheimer's disease in general is an incurable brain disease affecting middle aged and elderly people throughout the world. According to most recent estimates, it is the fourth or fifth leading cause of death among North Americans, and is responsible for inestimable personal and social tragedy, loss of productivity, and custodial burden to society. There is presently no widely-accepted effective treatment for Alzheimer's disease.

The principle symptom (manifestation) of Alzheimer's disease is the loss of higher mental faculties, typified by the loss of memory and behavior referred to as "dementia." Dementia is a symptom or syndrome that can be seen in many brain diseases other than Alzheimer's disease, such as stroke, encephalitis and metabolic diseases. Since memory loss and dementia are relatively nonspecific symptoms, a certain and specific definition of Alzheimer's disease is based on the characteristic microscopic state of the brain, described initially by Marinesco, Alzheimer and others. See Alzheimer, A., *Allegemeine Zeitschrift fur Psychiatrie* 64:146-148 (1907); Marinesco, G., *Comptes Rendus des Seances de la Societe de Biologie et ses Filiales* 70:606-608 (1911).

The particular microscopic features that are accepted indicators of Alzheimer's disease, and that separate Alzheimer's disease from other causes of dementia, are the accumulation of large numbers of brain lesions referred to as senile or amyloid plaques and neurofibrillary tangles. Senile or amyloid plaques are spherical, ranging from 10 to 200 μm in diameter, and while found only occasionally in aged adult cerebral cortex, are found in large numbers in Alzheimer-affected cortex. These lesions, when found in suitable quantity in a brain sample, are the definitive criteria for the diagnosis of Alzheimer's disease.

Amyloid plaques in large quantities are essentially found only in the Alzheimer group of diseases, whereas neurofibrillary tangles are nonspecific and are found in at least ten other neurological diseases. See Corsellis, J. A. N., GREENFIELD's NEUROPATHOLOGY 951-1025 (4th ed. 1984) (Edward Arnold, London). Individual amyloid plaques have roughly 1000× the volume of individual neurofibrillary tangles. True measurements of total brain amyloid plaque and neurofibrillary content are not available, but on the above basis it is likely that the volume of abnormal brain tissue occupied by amyloid plaques is many hundreds of times that of neurofibrillary tangles. The essential feature of the amyloid plaque is the presence of amyloid fibrils, which are a congophilic red-green birefringent microfibrillar material. Corsellis, loc. cit.

A microscopic structure referred to as the dense microsphere (DMS) is known to exist in normal brain and in brain affected by Alzheimer's disease. See Averback, *Acta Neuropathol.* 61:148-52 (1983); results confirmed by Hara, *J. Neuropath. Exp. Neurol.* 45(2):169-178 (1986). The DMS more recently have been called "spherons." "Spherons" in the context of the present invention therefore will denote the same thing as DMS, and refer to the spherical microscopic structure that exists in normal brain.

Some specialists believe that spherons are linked to cerebral amyloid plaques as the source of, or as a precursor to, the cerebral amyloid characteristic of Alzheimer's disease and related conditions. Evidence for the existence of spherons comes from microscopic histological section studies of fixed whole brain tissue. The spherons are observed as randomly dispersed, highly infrequent structures numbering ~$10^2$/mm$^3$.

Various components of spherons (e.g., "DMS") have previously been identified. It is known that the disintegration of spherons in the brain parenchyma is associated with the onset and progression of cerebral amyloid plaque formation that is characteristic of Alzheimer's disease and related conditions. More specifically, disintegration of spherons releases protein and non-protein components, or mixtures of protein and non-protein components. A portion of the spheron components form cerebral amyloid plaques, while other portions either remain in the brain, or are removed from the brain parenchyma via circulating bodily fluids, including cerebrospinal fluid, serum and the like.

It also is believed that spherons undergo a growth and bursting cycle bringing about a cataclysmic cascade of spheron bursts, and subsequent brain injury. As disclosed in U.S. Pat. No. 6,130,221, the disclosure of which is incorporated by reference herein in its entirety, an important mechanism of initiation and promotion of spheron disruption has been discovered that involves a distinctive autocatalytic phenomenon, whereby the disruption, degeneration, and evolution of an individual spheron into an individual cerebral amyloid plaque provides the stimulus for a group or field of other spherons to disrupt, degenerate and evolve in a recurring set of waves. This unchecked, autocatalytic phenomenon causes an exponential growth pattern: small, perhaps statistically insignificant differences (between individual brains) in starting numbers of disrupted spherons in situ evolve into statistically significant differences after generations of the cycle. For example, if all other factors were equal, a subject having an initial group of 100 spheron bursts would not be statistically or symptomatically different from a second subject having an initial group of 98 spheron bursts. However, if over time each of the initial spheron initiated 10 subsequent spherons to disrupt, each of which in turn initiated 10 subsequent spheron disruptions, then group 1 after 20 generations would have $2 \times 10^{20}$ more disrupted spherons than group 2, which is significant.

The description herein of any disadvantages of known compounds, systems, methods and apparatus is in no way intended to limit the present invention. Indeed, the present invention may employ one or more known compounds, systems, methods, and apparatus without suffering from the known disadvantages.

SUMMARY OF THE INVENTION

There remains a need in the art for new treatments for treating symptoms of AD not directly attributable to neurotransmitter deficits or to amyloid plaque formation. There also exists a need to develop methods for identifying therapies useful in treating such symptoms, as well as animal models useful in screening for therapies useful in treating these symptoms. The present invention satisfies these needs.

The present invention is premised in part on the surprising discovery that peptides containing amino acid sequences corresponding to components of spherons that are not directly attributable to amyloid plaque formation are toxic to neuronal cells, and are believed to cause other deleterious effects, including neuronal dysfunction. The invention also is premised in part on the discovery that these particular components, when released from the spherons, damage the brain in a manner that is distinguishable from the amyloid-producing effects. The invention also is premised in part on the discovery that these particular components may be racemized.

The invention also is premised on the discovery that these particular components in the concentrations present when released from the spherons, provide greatly increased activity on proprotein convertase 1 (PC1) inhibition, (as well as increased activity on proprotein convertases PC2-PC8), and furin, leading to decreased adrenocorticotrophic hormone (ACTH), insulin, αMSH, βendorphin, and enkephalin production, as well as decreased or otherwise altered thyrotropin-releasing hormone (TRF), dynorphin, pro-insulin, pro-glucagon, pro glucagon-like peptide (GLP), pro-somatostatin, pro-pancreatic peptide, pro-GHRH, neuropeptide melamin-concentrating hormone, NEI, neurotensin, opioid peptides, and other peptides and neuronal dysfunction. These components also provide increased neuropeptides from proSAAS domains. All of the above are believed to lead to a cascade of effects including but not limited to derangements of glucose production (insulin and ACTH), derangements of corticosteroid pathways (ACTH), derangements of thyroid pathways (TRH), derangements of enkephalins, derangements of other significant bioactive cerebral molecules and molecular pathways, as well as derangements of glucagon, GLP, somatostatin, pancreatic peptide, GHRH, neuropeptide melanin-concentrating hormone, NEI, neurotensin, and opioid peptides. In addition, greatly increased activity on proprotein convertase inhibition will affect the post-translational processing of proenzymes such as proBACE (beta-site APP cleaving enzyme, also known as beta-secretase) involved in the post-translational processing, modification and cleavage of amyloid precursor protein (APP). These above diverse biochemical pathway imbalances are well known to be disease producing and symptom producing. These imbalances are well known to produce behavioral, mental, and cognitive symptoms, the latter being similar to those found in neurodegenerative disorders, such as dementia and dementia associated with various types and Alzheimer's disease.

It has also been determined that the spheron protein components of the invention are highly racemized. In a racemized protein, one or more of the naturally occurring L stereoisomer forms of the protein's amino acid residues has been converted to a D stereoisomer form. All of the amino acids found in proteins, other than glycine, have a naturally occurring L stereoisomer form and a D stereoisomer form. Threonine and isoleucine also have diastereomer L-allo and D-allo forms. The extent of the racemization of the protein can provide an estimate of the protein's age. Racemization analysis of proteins and peptides released from spherons showed significant elevations of D-aspartate (5-9 mol % vs. 2 mol % in controls) and D-serine (2.0-2.4% vs. 0 mol % in controls). Racemized protein components also are included in the present invention.

In accordance with a feature of an embodiment of the present invention, there is provided a method of treating or ameliorating brain damage and/or any of the above described disorders that comprises administering to an animal in need thereof, a compound that prevents the cytotoxic effects, (and other deleterious effects described herein or later discovered), of a spheron component peptide other than a spheron component directly responsible for forming amyloid plaque, the spheron component peptide being one or more components selected from:

a) GEAAGAVQELAR; (SEQ ID NO. 1)

b) GLSAASPPLAETGAPR; (SEQ ID NO. 2)

c) ARAEAQEAEDQQAR; (SEQ ID NO. 3)

d) VLAQLLR; (SEQ ID NO. 4)

e) ALAHLLEAERQER; (SEQ ID NO. 5)

f) AADHDVGSELPPEGVLGALLR; (SEQ ID NO. 6)

g) LETPAPQVPAR; (SEQ ID NO. 7)

h) ILAGSADSEGVAAPR; (SEQ ID NO. 8)

i) ARPVKEPRGLSAASPPLAETGAPRRF; (SEQ ID NO. 9)

j) ARPVKEP; (SEQ ID NO. 10)

k) GLSAASPPLAETGAPRRF; (SEQ ID NO. 11)

```
l)    AADHDVGSELPPEGVLGALLRVKRLETPAPQVPA;    (SEQ ID NO. 12)

m)    AADHDVGSELPPEGVLGALLRV;                (SEQ ID NO. 13)

n)    LETPAPQVPA;                            (SEQ ID NO. 14)

o)    RRSVPRGEAAG;                           (SEQ ID NO. 15)

p)    VLAQLLRVWGAPRNSD;                      (SEQ ID NO. 16)

q)    PALGLDDDPDAPAAQLAR;                    (SEQ ID NO. 17)

r)    LARALLRARLDPAALAA;                     (SEQ ID NO. 18)

s)    QLVPAPVPAAALRPRPPVYDD;                 (SEQ ID NO. 19)

t)    GPAGPDAEEAGDE;                         (SEQ ID NO. 20)

u)    TPDVDPELLRYLLGR                        (SEQ ID NO. 21)

v)    LLRVKR; and                            (SEQ ID NO. 22)

w)    VLGALLRVKRLE                           (SEQ ID NO. 23)
``` wherein the spheron component peptide has been racemized. Preferably, at least one of the amino acid residues (other than glycine) of the spheron component peptide has: (i) been converted from an L stereoisomer form to a D stereoisomer form; (ii) been replaced by a D stereoisomer form; or (iii) otherwise undergone other steeoisomeric changes.

In accordance with another feature of an embodiment of the present invention, there is provided a composition comprising a compound that prevents the cytotoxic effects, (and other deleterious effects described herein or later discovered), of a spheron component peptide other than a spheron component responsible for forming amyloid plaque, the spheron component peptide being one or more components selected from the above group. The compound may be any of the proprotein convertases (PC1-PC8), furin, or one or more active sites on PC1 selected from the group consisting of:

```
ENKHG;              (SEQ ID NO. 24)

LDGIVTDAIE;         (SEQ ID NO. 25)

SWGPNDD;            (SEQ ID NO. 26)

WASGNG;             (SEQ ID NO. 27)

CDGYTDSIYTI; and    (SEQ ID NO. 28)

HTGTS.              (SEQ ID NO. 29)
```

In accordance with yet another feature of an embodiment of the invention, there is provided a method of screening for compounds useful in treating or ameliorating brain damage or any of the other disorders described above that comprises first culturing reproducible cells. The method also includes adding to the cells a spheron component peptide other than a spheron component responsible for forming amyloid plaque in a concentration sufficient to form an altered cell culture (e.g., by reducing the viability of the cells, by increasing the activity of the cells on prophormone convertase PC1- PC8 inhibition, and the like), and then administering to some of the altered cell cultures a test compound. Those test compounds that are effective in reducing or ameliorating the altered effect caused by the spheron component, when compared to controls that had no test compound administered, are useful in treating or ameliorating brain damage or any of the other disorders described above. The spheron component peptides preferably are one or more component selected from:

```
a)    GEAAGAVQELAR;                          (SEQ ID NO. 1)

b)    GLSAASPPLAETGAPR;                      (SEQ ID NO. 2)

c)    ARAEAQEAEDQQAR;                        (SEQ ID NO. 3)

d)    VLAQLLR;                               (SEQ ID NO. 4)

e)    ALAHLLEAERQER;                         (SEQ ID NO. 5)

f)    AADHDVGSELPPEGVLGALLR;                 (SEQ ID NO. 6)

g)    LETPAPQVPAR;                           (SEQ ID NO. 7)

h)    ILAGSADSEGVAAPR;                       (SEQ ID NO. 8)

i)    ARPVKEPRGLSAASPPLAETGAPRRF;            (SEQ ID NO. 9)

j)    ARPVKEP;                               (SEQ ID NO. 10)

k)    GLSAASPPLAETGAPRRF;                    (SEQ ID NO. 11)

l)    AADHDVGSELPPEGVLGALLRVKRLETPAPQVPA;    (SEQ ID NO. 12)

m)    AADHDVGSELPPEGVLGALLRV;                (SEQ ID NO. 13)

n)    LETPAPQVPA;                            (SEQ ID NO. 14)

o)    RRSVPRGEAAG;                           (SEQ ID NO. 15)

p)    VLAQLLRVWGAPRNSD;                      (SEQ ID NO. 16)

q)    PALGLDDDPDAPAAQLAR;                    (SEQ ID NO. 17)

r)    LARALLRARLDPAALAA;                     (SEQ ID NO. 18)

s)    QLVPAPVPAAALRPRPPVYDD;                 (SEQ ID NO. 19)

t)    GPAGPDAEEAGDE;                         (SEQ ID NO. 20)

u)    TPDVDPELLRYLLGR                        (SEQ ID NO. 21)

v)    LLRVKR; and                            (SEQ ID NO. 22)

w)    VLGALLRVKRLE                           (SEQ ID NO. 23)
``` wherein the spheron component peptide has been racemized. Preferably, at least one of the amino acid residues (other than glycine) of the spheron component peptide has: (i) been converted from an L stereoisomer form to a D stereoisomer form; (ii) been replaced by a D stereoisomer form; or (iii) otherwise undergone other steeoisomeric changes.

In accordance with another feature of an embodiment of the invention, there is provided an Alzheimer's Disease symptom animal model, or test animal, a method of making the animal model or test animal, and to a method of using the animal model or test animal to screen for effective therapies for treating or ameliorating brain damage caused by spheron components other than a spheron component directly responsible for forming amyloid plaque. The animal model comprises an animal having a gene inserted into the brain thereof, whereby the gene over-expresses one or more spheron component peptides selected from the group defined above. The test animal comprises an animal having one or more of the spheron component peptides selected from the group defined above administered thereto, whereby administration may be by intrathecal, intravenous, intra cerebral ventricular, or other administration routes. The method of making the animal model therefore includes preparing a gene that expresses one or more of spheron component peptides selected from the group defined above, incorporating the gene into the brain of an animal (e.g. by a transgenic mechanism, according to methods well known in the art), and inducing the gene to over-express the spheron component peptide. The method of making the test animal includes administering to the animal one or more of the spheron component peptides selected from the group defined above.

The method of using the animal model or test animal includes preparing a group of test animals, or preparing a group of animals having a gene in the brain thereof that over-expresses one or more of spheron component peptides selected from the group defined above, and then inducing the gene to over-express the spheron component peptide. The method includes administering to a select group of animals a test compound, sacrificing the animals, and then measuring the amount of isolated spheron component peptides present in the sacrificed animal's brain, and/or measuring the percentage of viable cells at or around the locus of the gene and/or measuring the injury of the brain in relation to the gene over-expression, and/or measuring any altered brain function, behavior, etc. in the animal. The method concludes by selecting those test compounds that reduce the amount of isolated spheron component peptides, when compared to controls, and/or by selecting those test compounds that yield a higher percentage of viable cells at or around the locus of the gene, when compared to controls having no test compound administered thereto, and/or by selecting those test compounds that yield less brain injury in relation to the gene over-expression compared to controls, and/or by selecting those test compounds that result in improved brain function, behavior, etc. compared to controls.

These and other features of various embodiments of the present invention will be readily apparent to one of ordinary skill in the art upon a review of the detailed description of the invention, including the examples.

DETAILED DESCRIPTION OF THE PREFERRED EMBODIMENTS

Terms and phrases used herein are defined as set forth below unless otherwise specified. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the compounds, molecules, cell lines, vectors, and methodologies that are reported in the publications and that might be used in connection with the invention. Nothing herein is to be construed as an admission that the invention is not entitled to antedate such disclosure by virtue of prior invention.

Throughout this description, the phrase "Alzheimer's disease and related conditions" denotes conditions classified under the rubric "cerebral amyloidosis." Such conditions include, but are not limited to Alzheimer's disease [pre-senile dementia, senile dementia]; Alzheimer's disease associated with Down's syndrome; Alzheimer's disease associated with other central-nervous-system diseases, such as Parkinson's disorder; congophilic angiopathy [associated or not associated with Alzheimer's disease], and other dimentia such as Frontotemporal Dimentia (FTD), mild cognitive impairment, and the like. Throughout this description, the phrase "DMS components" or "spheron components" denotes any component of DMS, protein, non-protein, or mixtures of protein and non-protein, originating from the internal or central region or from the outer membrane portion of DMS. Throughout this description, the phrase "disrupting" or "digesting a suspension comprising DMS" denotes any process whereby DMS are broken down into DMS components.

"Spheron components" are referred to herein as components of spherons, (formerly DMS), and include those specifically described herein, as well as any and all components described in U.S. Pat. Nos. 6,309,892, and 5,525,339, the disclosures of which are incorporated by reference herein in their entirety.

As used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Amino acids and amino acid residues described herein may be referred to according to the accepted one or three-letter code provided in the table below. These amino acids or residues described herein are of the naturally occurring L stereoisomer form, and also include the racemized D stereoisomer form.

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |

-continued

| Amino Acid | One-Letter Symbol | Three-Letter Symbol |
|---|---|---|
| Threonine | T | Thr |
| Tryptophan | W | Trp |
| Tyrosine | Y | Tyr |
| Valine | V | Val |

The term "fragment" as it is used herein refers to a protein or polypeptide that consists of a continuous subsequence of the subject amino acid sequence or subject molecule, and includes naturally occurring fragments such as splice variants and fragments resulting from naturally occurring in vivo protease activity. "Subject amino acid sequence" and "subject molecule" denotes the amino acid sequence or molecule that is fragmented or otherwise modified herein. Such a fragment may be truncated at the amino terminus, the carboxy terminus, and/or internally (such as by natural splicing). Such fragments may be prepared with or without an amino terminal methionine. The term "fragment" includes fragments, whether identical or different, from the subject amino acid sequence, with a contiguous amino acid sequence in common or not, joined together, either directly or through a linker.

The term "variant" refers to a protein or polypeptide in which one or more amino acid substitutions, deletions, and/or insertions are present as compared to the subject amino acid sequence or subject molecule and includes naturally occurring allelic variants or alternative splice variants thereof. The term "variant" includes the replacement of one or more amino acids in a peptide sequence with a similar or homologous amino acid(s) or a dissimilar amino acid(s). There are many scales on which amino acids can be ranked as similar or homologous. (Gunnar von Heijne, *Sequence Analysis in Molecular Biology*, p. 123-39 (Academic Press, New York, N.Y. 1987.) Preferred variants include alanine substitutions at one or more of amino acid positions. Other preferred substitutions include conservative substitutions that have little or no effect on the overall net charge, polarity, or hydrophobicity of the protein. Conservative substitutions are set forth in Table 1 below.

TABLE 1

Conservative Amino Acid Substitutions

| | |
|---|---|
| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | proline |
| | methionine |
| | leucine |
| | isoleucine |

Table 2 sets forth another scheme of amino acid substitution:

TABLE 2

| Original Residue | Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include the subject amino acid sequences or subject molecules with additional amino acid residues before or after the subject entity on linker peptides. For example, a cysteine residue may be added at both the amino and carboxy terminals in order to allow the cyclisation by the formation of a di-sulphide bond. The term "variant" also encompasses polypeptides that have the amino acid sequence of a subject amino acid sequence or subject molecule with at least one and up to 25 or more additional amino acids flanking either the 3' or 5' end of the subject entity.

The term "derivative" refers to a chemically modified protein or polypeptide that has been chemically modified either by natural processes, such as processing and other post-translational modifications, but also by chemical modification techniques, such as, for example, by addition of one or more polyethylene glycol molecules, sugars, phosphates, and/or other such molecules, where the molecule or molecules are not naturally attached to the wild-type subject amino acid sequence or subject molecule. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide. Also, a given protein or polypeptide may contain many types of modifications.

Modifications can occur anywhere in a protein or polypeptide, including the peptide backbone, the amino acid sidechains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for example, *Proteins—Structure And Molecular Properties,* 2nd Ed., T. E. Creighton, W. H. Freeman and Company, New York (1993) and Wold, F., "Posttranslational Protein Modifications: Perspectives and Prospects," pgs. 1-12 in *Posttranslational Covalent Modification Of Proteins,* B. C. Johnson, Ed., Academic Press, New York (1983); Seifter et al., *Meth. Enzymol.* 182: 626-646 (1990) and Rattan et al., "Protein Synthesis: Posttranslational Modifications and Aging," *Ann. N.Y. Acad. Sci.* 663: 48-62 (1992). The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well.

The term "homologue" refers to a protein or peptide that is at least 60 percent identical in its amino acid sequence, as determined by standard methods that are commonly used to compare the similarity in position of the amino acids of two polypeptides. The degree of similarity or identity between two proteins can be readily calculated by known methods, including but not limited to those described in *Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; *Sequence Analysis Primer,* Gribskov, M. and Devereux, J., eds., M Stockton Press, New York, 1991; and Carillo H. and Lipman, D., SIAM, *J. Applied Math.,* 48: 1073 (1988). Preferred methods to determine identity are designed to give the largest match between the sequences tested. Methods to determine identity and similarity are codified in publicly available computer programs.

Preferred computer program methods useful in determining the identity and similarity between two sequences include, but are not limited to, the GCG program package (Devereux, J., et al., *Nucleic Acids Research,* 12(1): 387 (1984)), BLASTP, BLASTN, and FASTA, Atschul, S. F. et al., *J. Molec. Biol.,* 215: 403-410 (1990). The BLAST X program is publicly available from NCBI and other sources (BLAST Manual, Altschul, S., et al., NCBI NLM NIH Bethesda, Md. 20894; Altschul, S., et al., *J. Mol. Biol.,* 215: 403-410 (1990). By way of example, using a computer algorithm such as GAP (Genetic Computer Group, University of Wisconsin, Madison, Wis.), the two proteins or polypeptides for which the percent sequence identity is to be determined are aligned for optimal matching of their respective amino acids (the "matched span", as determined by the algorithm).

A gap opening penalty (which is calculated as 3× (times) the average diagonal; the "average diagonal" is the average of the diagonal of the comparison matrix being used; the "diagonal" is the score or number assigned to each perfect amino acid by the particular comparison matrix) and a gap extension penalty (which is usually 1/10 times the gap opening penalty), as well as a comparison matrix such as PAM 250 or BLOSUM 62 are used in conjunction with the algorithm. A standard comparison matrix (see Dayhoff et al. in: *Atlas of Protein Sequence and Structure,* vol. 5, supp. 3 [1978] for the PAM250 comparison matrix; see Henikoff et al., *Proc. Natl. Acad. Sci USA,* 89:10915-10919 [1992] for the BLOSUM 62 comparison matrix) also may be used by the algorithm. The percent identity then is calculated by the algorithm. Homologues will typically have one or more amino acid substitutions, deletions, and/or insertions as compared with the subject amino acid sequence or subject molecule.

The term "combinations" insofar as it refers to combinations of the peptides described herein, denotes various permutations and combinations of two or more peptides. For example a combination could include the combination of SEQ ID NOS. 1-4, bonded head to tail, or the final 7 amino acids of SEQ ID NO. 1 together with the first 5 amino acides of SEQ ID NO. 2, and the like.

The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). In the context of this invention, the expression peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to this invention provide a spatial arrangement of reactive chemical moieties that closely resemble the three-dimensional arrangement of active groups in the subject amino acid sequence or subject molecule on which the peptide mimetic is based. As a result of this similar active-site geometry, the peptide mimetic has effects on biological systems that are similar to the biological activity of the subject entity.

The peptide mimetics of this invention are preferably substantially similar in both three-dimensional shape and biological activity to the subject entitites described herein. Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. An example is described in the paper "Tritriated D-ala$^1$-Peptide T Binding", Smith C. S. et al., *Drug Development Res.,* 15, pp. 371-379 (1988). A second method is altering cyclic structure for stability, such as N to C interchain imides and lactames (Ede et al. in Smith and Rivier (Eds.) "Peptides: Chemistry and Biology", *Escom, Leiden* (1991), pp. 268-270). An example of this is provided in conformationally restricted thymopentin-like compounds, such as those disclosed in U.S. Pat. No. 4,457,489 (1985), Goldstein, G. et al., the disclosure of which is incorporated by reference herein in its entirety. A third method is to substitute peptide bonds in the subject entity by pseudopeptide bonds that confer resistance to proteolysis.

A number of pseudopeptide bonds have been described that in general do not affect peptide structure and biological activity. One example of this approach is to substitute retro-inverso pseudopeptide bonds ("Biologically active retro-inverso analogues of thymopentin", Sisto A. et al in Rivier, J. E. and Marshall, G. R. (eds) "Peptides, Chemistry, Structure and Biology", *Escom, Leiden* (1990), pp. 722-773) and Dalpozzo, et al. (1993), *Int. J. Peptide Protein Res.*, 41:561-566, incorporated herein by reference). According to this modification, the amino acid sequences of the peptides may be identical to the sequences of a subject amino acid sequence or subject molecule described herein, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond (Couder, et al. (1993), *Int. J. Peptide Protein Res.*, 41:181-184, incorporated herein by reference in its entirety).

Thus, the amino acid sequences of these peptides may be identical to the sequences of the subject amino acid sequence, except that one or more of the peptide bonds are replaced by an isostere pseudopeptide bond. The expression "amino acid sequence(s)" preferably is used herein to denote a sequence of at least two amino acids, preferably at least four, and more preferably at least five. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of the subject amino acid sequences and subject molecules represent another class of peptide mimetics that retain the important structural determinants for biological activity, yet eliminate the peptide bonds, thereby conferring resistance to proteolysis (Simon, et al., 1992, *Proc. Natl. Acad. Sci. USA*, 89:9367-9371, incorporated herein by reference in its entirety). Peptoids are oligomers of N-substituted glycines. A number of N-alkyl groups have been described, each corresponding to the side chain of a natural amino acid (Simon, et al. (1992), cited above). Some or all of the amino acids of the subject amino acid sequences may be replaced with the N-substituted glycine corresponding to the replaced amino acid.

A "composition comprising a given molecule" (e.g., antibody, bispecific antibody, or diabody) or a "composition comprising a given amino acid sequence," as these terms are used herein, refer broadly to any composition containing the given molecule, polynucleotide or amino acid sequence. The composition may comprise a dry formulation, an aqueous solution, a solution in a non-aqueous solvent, or a sterile composition. The compositions may be stored in freeze-dried form and may be associated with a stabilizing agent such as a carbohydrate. In hybridizations and other applications, the compositions may be deployed in an aqueous solution containing salts, e.g., NaCl, detergents, e.g., sodium dodecyl sulfate (SDS), and other components, e.g., Denhardt's solution, dry milk, salmon sperm DNA, etc.

Throughout this description and in the appended claims, reference to a "peptide," a "spheron component peptide," and specific amino acid sequences include those sequences specifically identified, and include fragments, variants, derivatives, homologues, combinations, mimetics, and racemizations thereof.

Throughout this description, the expressions "specific binding" or "specifically binding," "binding," "binds," and/or "recognizes" refer to the interaction between a molecule, protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The present inventor has found that certain spheron component peptides that are not the spheron component peptides directly attributable to amyloid plaque formation, are, inter alia, cytotoxic. The inventor has found that these particular spheron component peptides reduce the viability of brain cells. The cytotoxic effects of these spheron component peptides, when released in the brain of an animal, are believed to cause brain damage, neuronal dysfunction, and Alzheimer's Disease symptoms that are distinguishable from amyloid-producing effects. Based on this discovery, and not intending on being bound by any theory of production or operation, the present inventor believes that reducing and/or preventing the cytotoxicity and/or neuronal dysfunction of the spheron component peptides will prevent and/or ameliorate at least one or more symptoms of Alzheimer's Disease, or dementia associated with cerebral amyloidosis.

The present inventor also believes that the presence of these particular spheron components in the concentrations in which they are released from the spherons may be the cause of many other adverse affects. The spheron component peptides described herein are similar to, and consistent with portions of a protein referred to as proSAAS, which is known as a granin-like neuroendocrine peptide precursor. Pro SAAS is active at a tissue concentration of 1 nM. ProSAAS derived from spherons is present in the brain in spherons at a brain concentration much higher than 1 nM. It is believed that racemized proSAAS also is present in the brain in spherons. Optically active amino acids usually are racemized (converted to D-L mixtures) when a chiral carbon passes through a symmetrical intermediate. While not intending on being bound by any theory of operation, it is believed that over time, the pro-SAAS, and peptide component peptides described herein that are present in spherons become racemized. It is known that L-isoaspartyl and D-aspartyl residues result from the spontaneous degradation of L-aspartate and L-asparagine residues of proteins over time. Clarke, S., *Int. J. Pept. Protein Res.* Vol. 30, pp 808-821 (1987).

At the concentrations described above, proSAAS and the spheron component peptides described herein, as well as racemized forms thereof, provide greatly increased activity on proprotein convertase 1 (PC1) inhibition, (as well as increased activity on proprotein convertases PC2-PC8), and furin, leading to decreased adrenocorticotrophic hormone (ACTH), insulin, αMSH, βendorphin, and enkephalin production, as well as decreased or otherwise altered thyrotropin-releasing hormone (TRF), dynorphin, pro-insulin, pro-glucagon, pro-glucagon-like peptide (GLP) pro-somatostatin, pro-pancreatic peptide, pro-GHRH, neuropeptide melamin-concentrating hormone, NEI, neurotensin, opioid peptides, and other peptides, and neuronal dysfunction. In addition, greatly increased activity on proprotein convertase inhibition will affect the post-translational processing of proenzymes such as proBACE (beta-site APP cleaving enzyme, also known as beta-secretase) involved in the post-translational processing, modification and cleavage of amyloid precursor protein (APP). These components also provide increased neuropeptides from proSAAS domains. All of the above are believed to lead to a cascade of effects including but not limited to derangements of glucose production (insulin and ACTH), derangements of corticosteroid pathways (ACTH), derangements of thyroid pathways (TRH), derangements of enkephalins, derangements of other significant bioactive cerebral molecules and molecular pathways, as well as derangements of glucagon, somatostatin, pancreatic peptide, GHRH, neuropeptide melanin-concentrating hormone, NEI, neurotensin, and opioid peptides. These above diverse biochemical pathway imbalances are well known to be disease producing and symptom producing. These imbalances are well known to produce behavioral and mental and cognitive symptoms, the latter being similar to those found in neurodegenerative disorders, such as dementia of various types and Alzheimer's disease.

The present inventor therefore believes that abnormally elevated proSAAS concentrations derived from spherons will be pharmacologically blocked by compounds that will be effective in ameliorating or attenuating the harmful effects of the abnormally elevated quantities of proSAAS in the brain. It is further envisaged that abnormally elevated proSAAS concentrations derived from spherons will be pharmacologically blocked by compounds that will be effective in ameliorating or attenuating the harmful effects of the decreased breakdown of pro-opiomelanocortin (POMC) brought about by the abnormally elevated quantities of proSAAS in the brain in relation to the spherons. It is further envisaged that abnormally elevated proSAAS concentrations derived from spherons will be pharmacologically blocked by compounds that will be effective in ameliorating or attenuating the harmful effects of the elevated levels of molecules and pathways related to ACTH, insulin, and enkephalins, brought about by the abnormally elevated quantities of proSAAS in the brain.

The present inventor also believes that the presence of spheron component peptides that are similar to and consistent with portions of proSAAS in live tissue not only is an indication of the disruption of spherons, and hence the onset of cerebral amyloidosis, as previously reported, but it also is toxic insofar as it causes other live tissue cell death. The presence of these spheron component peptides also will have greatly increased activity on PC1 and PC2 inhibition, leading to decreased ACTH, insulin, and enkephalin production; as well as decreased TRF, dynorphin, and other peptides. The presence of proSAAS or fragments thereof at these concentrations also will lead to increased neuropeptides from proSAAS domains.

The present inventor believes that spheron component peptides present in live mammalian brain tissue is a marker for cerebral amyloidosis, and that it exacerbates cerebral amyloidosis by causing cell necrosis in the live tissue in which it exists. Accordingly, it is believed that, as a mammal becomes inflicted with cerebral amyloidosis, spherons begin to disrupt, burst, and/or otherwise disintegrate thereby producing spheron component peptides. The present inventor believes that some of the spheron component peptides so produced are believed to be precursors to harmful amyloid protein, while other spheron component peptides begin destroying other live tissue without forming amyloid (e.g., other nerve cells and brain tissue) in the vicinity of the spheron component, thereby exacerbating the progression of the disease. These conditions are in addition to the other conditions described above that are caused by the increased abnormally high concentrations of proSAAS, or fragments thereof, that are believed to be released from the spherons.

The invention therefore relates to a method of treating or ameliorating brain damage and other disorders that comprises administering to an animal in need thereof, a compound that prevents the cytotoxic effects, (and other deleterious effects described herein or later discovered), of a spheron component peptide other than a spheron component directly responsible for forming amyloid plaque, the spheron component peptide being one or more component selected from, as well as variants, derivatives, homologues, and peptide mimetics thereof:

```
                                        (SEQ ID NO. 1)
    GEAAGAVQELAR;

(SEQ ID NO. 2)
    GLSAASPPLAETGAPR;

(SEQ ID NO. 3)
    ARAEAQEAEDQQAR;

(SEQ ID NO. 4)
    VLAQLLR;

(SEQ ID NO. 5)
    ALAHLLEAERQER;

(SEQ ID NO. 6)
    AADHDVGSELPPEGVLGALLR;

(SEQ ID NO. 7)
    LETPAPQVPAR;

(SEQ ID NO. 8)
    ILAGSADSEGVAAPR;

(SEQ ID NO. 9)
    ARPVKEPRGLSAASPPLAETGAPRRF;

(SEQ ID NO. 10)
    ARPVKEP;

(SEQ ID NO. 11)
    GLSAASPPLAETGAPRRF;

(SEQ ID NO. 12)
    AADHDVGSELPPEGVLGALLRVKRLETPAPQVPA;

(SEQ ID NO. 13)
    AADHDVGSELPPEGVLGALLRV;

(SEQ ID NO. 14)
    LETPAPQVPA;

(SEQ ID NO. 15)
    RRSVPRGEAAG;

(SEQ ID NO. 16)
    VLAQLLRVWGAPRNSD;

(SEQ ID NO. 17)
    PALGLDDDPDAPAAQLAR;

(SEQ ID NO. 18)
    LARALLRARLDPAALAA;

(SEQ ID NO. 19)
    QLVPAPVPAAALRPRPPVYDD;

(SEQ ID NO. 20)
    GPAGPDAEEAGDE;
```

-continued

```
                              (SEQ ID NO. 21)
TPDVDPELLRYLLGR;

(SEQ ID NO. 22)
LLRVKR; and (SEQ ID NO. 23)
VLGALLRVKRLE,
``` wherein the spheron component peptide has been racemized. Preferably, at least one of the amino acid residues (other than glycine) of the spheron component peptide has: (i) been converted from an L stereoisomer form to a D stereoisomer form; (ii) been replaced by a D stereoisomer form; or (iii) otherwise undergone other steeoisomeric changes.

The methods and compositions of the invention are effective in treating disorders, including Alzheimer's disease, vascular dementia or multi-infarct dementia, dementia with Lewy bodies, Parkinson's disease, Pick's disease, Frontotemporal Dementia (FTD), and mild cognitive impairment. The inventive composition therefore includes a pharmaceutically effective amount of a compound that counteracts the effects of the release of proSAAS or peptide fragments thereof by spherons in the brain. Counteracting the effects of such spheron components can be accomplished in many ways, but the end result is to render such spheron components inactive (or by off-setting their deleterious effects) in one form or another. The composition preferably counteracts the effects of: (i) abnormally inhibited activity of proprotein convertases 1-8 (PC1-PC8) and furin in the brain or in other neuroendocrine tissues caused by the release of proSAAS or peptide fragments thereof from spherons in the brain; (ii) abnormally decreased adrenocorticotrophic hormone (ACTH) caused by the release of proSAAS or peptide fragments thereof from spherons in the brain; (iii) abnormally decreased insulin caused by the release of proSAAS or peptide fragments thereof from spherons in the brain; (iv) abnormally decreased enkephalins caused by the release of proSAAS or peptide fragments thereof from spherons in the brain; (v) abnormally decreased thyrotropin-releasing hormone (TRH) caused by the release of proSAAS or peptide fragments thereof from spherons in the brain; (vi) abnormally decreased dynorphin caused by the release of proSAAS or peptide fragments thereof from spherons in the brain; and (vii) abnormally increased effects such as neurotensin effects and cell signaling effects caused by abnormally increased other proSAAS fragments described herein.

The compositions, methods, and compounds of the invention also are effective in reducing or counteracting the inhibition of PC1 or other convertases (e.g., PC2-PC8, SPC3) and furin, caused by the release of proSAAS or peptide fragments thereof from spherons in the brain. It is preferred that the compounds, compositions, and methods of the invention counteract the effects of the release of proSAAS or peptide fragments from spherons in the brain by increasing or otherwise altering: (i) cerebral ACTH; (ii) cerebral insulin; (iii) cerebral enkephalins; (iv) cerebral TRH; (v) cerebral dynorphin; (vi) cerebral αMSH and βendorphin; (vii) cerebral proinsulin; (viii) cerebral pro-glucagon; (ix) cerebral pro-somatostatin; (x) cerebral pro-pancreatic peptide; (xi) cerebral pro-GHRH; (xii) cerebral neuropeptide melamin-concentrating hormone; (xiii) cerebral NEI; (xiv) cerebral neurotensin; and (xv) cerebral opioid peptides, and the like.

The above-mentioned levels can be increased by adding the specific component listed above, and consequently, the compositions and methods of the invention include one or more of the above-listed components, such as a proprotein convertase, fragment, domain or subunit thereof, whereby the proprotein convertase has an affinity for the proSAAS or peptide fragments released from spherons in the brain (e.g., SEQ ID NOS. 1-23). The compositions also may include an antibody, antibody fragment or short chain antibody that has an affinity for the proSAAS or peptide fragments released from spherons in the brain (e.g., SEQ ID NOS. 1-23). In addition, the compositions of the invention may include compounds that counteract the inhibition of PC1 by addition of PC1, or one or more active sites of PC! selected from the group consisting of:

```
ENKHG;              (SEQ ID NO. 24)

LDGIVTDAIE;         (SEQ ID NO. 25)

SWGPNDD;            (SEQ ID NO. 26)

WASGNG;             (SEQ ID NO. 27)

CDGYTDSIYTI; and    (SEQ ID NO. 28)

HTGTS.              (SEQ ID NO. 29)
```

As mentioned previously, the spheron component peptides listed above are similar to, and consistent with all or portions of a protein referred to as pro-SAAS, which is known as a granin-like neuroendocrine peptide precursor. The identification and characterization of pro-SAAS is described in Fricker, L. D., et al., "Identification and Characterization of pro-SAAS, a Granin-Like Neuroendocrine Peptide Precursor that Inhibits Prohormone Processing," *J. Neurosci*, 20(2):639-648 (2000). It is believed that pro-SAAS is linked to obesity in animals. It was not heretofore known that proSAAS or any of the possible peptides that form a portion of pro-SAAS had any relation to spherons, or any cytotoxic affect on brain cells or any relation to Alzheimer's disease, dementia, or cerebral amyloidosis. It also was not heretofore known that any of the possible peptides that form all or a portion of pro-SAAS were released by, or otherwise derived from spherons in concentrations high enough to cause any of a number deleterious effects.

In accordance with another feature of an embodiment of the present invention, there is provided a composition comprising a compound that does one or more of: (i) impedes or prevents the release of proSAAS or a peptide fragment thereof from a spheron; (ii) binds to, inhibits, antagonizes or competes with proSAAS or a peptide fragment thereof released from a spheron; or (iii) reduces or prevents the cytotoxic or other deleterious effects of proSAAS or a peptide fragment thereof released from a spheron, where by the pro-SAAS or peptide fragment thereof is a spheron component peptide other than a spheron component responsible for forming amyloid plaque, the spheron component peptide being one or more of the components selected from the above group.

The spheron component peptides described above can be isolated and purified using techniques known and described in the aforementioned articles, as well as those described in U.S. Pat. Nos. 5,525,339, and 6,309,892. Spherons may be derived form mammalian brain tissue and characterized, in essentially homogeneous form, by a range of diameters from about 0.1 μm to about 15 μm, and by certain stainability properties. In this regard, "homogeneous" means that the spherons represent the only structure discernible in the subject composition at the light-microscopic level. For example, the microspheric bodies of the present invention are homogeneously electron-dense when stained with osmium and lead, and can be visualized by thin-section electron microscopy; under optical microscopic examination, they appear eosinophilic and phloxinophilic, and are nonbirefringent when stained with Congo Red. When the microspheric bodies of the present invention are disrupted or disintegrated or digested, a material is produced that displays congophilic birefringence; that is, when stained with Congo Red the material becomes optically anisotropic to the extent of splitting an incident light wave into two waves with mutually perpendicular vibrational planes. Amyloid protein can also be detected by immunological labeling methods in spherons.

The spherical, intracellular spherons typically are found in human and other mammalian brains in gray-matter neuropil, where the spherical structures are enclosed in tiny, neuronal cellular processes. Spherons usually are solitary, non-perikayal and non-confluent, and are not easily found in cerebellum or in white matter. With regard to inter-spheron distances, the spatial distribution of spherons in grey matter regions is random. Compositions of spherons in homogeneous form can be produced by extraction to produce homogeneous samples of globular bodies according to procedures described in U.S. Pat. Nos. 4,816,416 and 5,231,170, the entire contents of which are incorporated by reference herein. Spherons contain amyloid.

The homogeneous composition of spherons prepared according to the above-described procedure can be disrupted by procedures described in the aforementioned U.S. Pat. Nos. 4,816,416 and 5,231,170, and then subjected to differential gradient centrifugation. Materials isolated in distinct sedimentation layers are stained with Congo Red. The present inventor believes that the spheron components are primarily responsible for the formation of cerebral amyloid plaques. The protein components of spheron membranes can be isolated by conventional extraction methods. Further analysis of spheron components can be accomplished by extraction of such components and by conventional methods such as chromatography that are well-known to those of ordinary skill in the art.

Spherons can be treated by a variety of methods to yield spheron components suitable for use according to the present invention. Exemplary of these methods are: (a) PAGE buffer solutions including TRIS, glycerol, .beta.-mercaptoethanol, bromophenol blue and sodium dodecyl sulfate (SDS), (b) ultrasonication and (c) other proteolytic treatments such as treating with various combinations of 0.25M acetic acid, 6M guanidine HCl, formic acid, 6M urea, pepsin and cyanogen bromide. The resulting homogeneous composition of spheron components can be further refined by isolating the components according to their molecular weight by polyacrylamide gel electrophoresis (PAGE) or according to the degree of their hydrophobicity by reverse phase high performance liquid chromatography (rpHPLC). Spheron components isolated by PAGE can be further characterized as either discrete migrating or non-migrating components. Spheron components also can be extracted from cerebrospinal fluid and other bodily fluids using the extraction procedures described above.

Among the numerous spheron components extracted in accordance with the procedures outlined herein, the particular spheron component peptides that are cytotoxic in tissue culture, and are believed to be cytotoxic in vivo to neuronal cells are listed below:

```
Spheron Component peptide #1
GEAAGAVQELAR                               [SEQ ID NO 1]

Gly-Glu-Ala-Ala-Gly-Ala-Val-Gln-Glu-

Leu-Ala-Arg
```

```
-continued
Spheron Component peptide #2
GLSAASPPLAETGAPR                           [SEQ ID NO 2]

Gly-Leu-Ser-Ala-Ala-Ser-Pro-Pro-Leu-

Ala-Glu-Thr-Gly-Ala-Pro-Arg

Spheron Component peptide #3
ARAEAQEAEDQQAR                             [SEQ ID NO 3]

Ala-Arg-Ala-Glu-Ala-Gln-Glu-Ala-Glu-

Asp-Gln-Gln-Ala-Arg

Spheron Component peptide #4
VLAQLLR                                    [SEQ ID NO 4]

Val-Leu-Ala-Gln-Leu-Leu-Arg

Spheron Component peptide #5
ALAHLLEAERQER                              [SEQ ID NO 5]

Ala-Leu-Ala-His-Leu-Leu-Glu-Ala-Glu-

Arg-Gln-Glu-Arg

Spheron Component peptide #6
AADHDVGSELPPEGVLGALLR                      [SEQ ID NO 6]

Ala-Ala-Asp-His-Asp-Val-Gly-Ser-Glu-

Leu-Pro-Pro-Glu-Gly-Val-Leu-Gly-Ala-

Leu-Leu-Arg

Spheron Component peptide #7
LETPAPQVPAR                                [SEQ ID NO 7]

Leu-Glu-Thr-Pro-Ala-Pro-Gln-Val-Pro-

Ala-Arg

Spheron Component peptide #8
ILAGSADSEGVAAPR                            [SEQ ID NO 8]

Ile-Leu-Ala-Gly-Ser-Ala-Asp-Ser-Glu-

Gly-Val-Ala-Ala-Pro-Arg

Spheron Component peptide #9
ARPVKEPRGLSAASPPLAETGAPRRF                 [SEQ ID NO 9]

Ala-Arg-Pro-Val-Lys-Glu-Pro-Gly-Leu-

Ser-Ala-Ala-Ser-Pro-Pro-Leu-Ala-Glu-

Thr-Gly-Ala-Pro-Arg-Arg-Phe

Spheron Component peptide #10
ARPVKEP                                    [SEQ ID NO 10]

Ala-Arg-Pro-Val-Lys-Glu-Pro

Spheron Component peptide #11
GLSAASPPLAETGAPRRF                         [SEQ ID NO 11]

Gly-Leu-Ser-Ala-Ala-Ser-Pro-Pro-Leu-

Ala-Glu-Thr-Gly-Ala-Pro-Arg-Arg-Phe

Spheron Component peptide #12
AADHDVGSELPPEGVLGALLRVKRLETPAPQVPA         [SEQ ID NO 12]

Ala-Ala-Asp-His-Asp-Val-Gly-Ser-Glu-

Leu-Pro-Pro-Glu-Gly-Val-Leu-Gly-Ala-

Leu-Leu-Arg-Val-Lys-Arg-Leu-Glu-Thr-

Pro-Ala-Pro-Gln-Val-Pro-Ala
```

```
Spheron Component peptide #13
AADHDVGSELPPEGVLGALLRV              [SEQ ID NO 13]

Ala-Ala-Asp-His-Asp-Val-Gly-Ser-Glu-

Leu-Pro-Pro-Glu-Gly-Val-Leu-Gly-Ala-

Leu-Leu-Arg-Val

Spheron Component peptide #14
LETPAPQVPA                          [SEQ ID NO 14]

Leu-Glu-Thr-Pro-Ala-Pro-Gln-Val-Pro-

Ala

Spheron Component peptide #15
RRSVPRGEAAG                         [SEQ ID NO 15]

Arg-Arg-Ser-Val-Pro-Arg-Gly-Glu-Ala-

Ala-Gly

Spheron Component peptide #16
VLAQLLRVWGAPRNSD                    [SEQ ID NO 16]

Val-Leu-Ala-Gln-Leu-Leu-Arg-Val-Trp-

Gly-Ala-Pro-Arg-Asn-Ser-Asp

Spheron Component peptide #17
PALGLDDDPDAPAAQLAR                  [SEQ ID NO 17]

Pro-Ala-Leu-Gly-Leu-Asp-Asp-Asp-Pro-

Asp-Ala-Pro-Ala-Ala-Gln-Leu-Ala-Arg

Spheron Component peptide #18
LARALLRARLDPAALAA                   [SEQ ID NO 18]

Leu-Ala-Arg-Ala-Leu-Leu-Arg-Ala-Arg-

Leu-Asp-Pro-Ala-Ala-Leu-Ala-Ala

Spheron Component peptide #19
QLVPAPVPAAALRPRPPVYDD               [SEQ ID NO 19]

Gln-Leu-Val-Pro-Ala-Pro-Val-Pro-Alaala-Ala-Leu-Arg-Pro-Arg-Pro-Pro-Val-

Tyr-Asp-Asp

Spheron Component peptide #20
GPAGPDAEEAGDE                       [SEQ ID NO 20]

Gly-Pro-Ala-Gly-Pro-Asp-Ala-Glu-Glu-

Ala-Gly-Asp-Glu

Spheron Component peptide #21
TPDVDPELLRYLLGR                     [SEQ ID NO 21]

Thr-Pro-Asp-Val-Asp-Pro-Glu-Leu-Leu-

Arg-Tyr-Leu-Leu-Gly-Arg

Spheron Component peptide #22
LLRVKR                              [SEQ ID NO 22]

Leu-Leu-Arg-Val-Lys-Arg

Spheron Component peptide #23
VLGALLRVKRLE                        [SEQ ID NO 23]

Val-Leu-Gly-Ala-Leu-Leu-Arg-Val-Lys-

Arg-Leu-Glu
``` wherein the spheron component peptide has been racemized. Preferably, at least one of the amino acid residues (other than glycine) of the spheron component peptide has: (i) been converted from an L stereoisomer form to a D stereoisomer form; (ii) been replaced by a D stereoisomer form; or (iii) otherwise undergone other steeoisomeric changes.

The afore-mentioned spheron component peptides can be used to identify compounds or combinations and mixtures thereof that are useful in preventing or reducing the effects of these peptides in the brain. Preventing or reducing the effects of these spheron component peptides will serve to treat and/or ameliorate symptoms that are believed to be the same symptoms associated with Alzheimer's Disease, but which are not brought about by amyloid plaque formation. Preventing or reducing the effects of these spheron component peptides also will serve to treat and/or ameliorate many other symptoms of Alzheimer's Disease and other disorders brought about by the presence of these spheron components in such high concentrations in the brain at or near the loci of the spherons.

One aspect of the invention entails a method of identifying compounds useful in treating and/or ameliorating the above-described symptoms by culturing reproducible cells, preferably tumor-forming cells, more preferably, glioma and neuroblastoma cells, adding at least one spheron component peptide to the cell culture, and then adding a test compound to some of the cell cultures. The method then entails measuring the percentage of viable cells, and then comparing the percentage of viable cells found with the cell cultures to which test compounds were added with the percentage of viable cells found in control cell cultures to which no test compounds were added. Useful test compounds are identified as those compounds used in the afore-mentioned example, whereby the cultures have a statistically significant greater number of viable cells than the control (e.g., no compound administered).

Another method of identifying useful compounds is to culture reproducible cells that are capable of expressing one or more of the cerebral components selected from cerebral ACTH, cerebral insulin, cerebral enkephalins, cerebral TRH, cerebral dynorphin, cerebral αMSH and βendorphin, cerebral pro-insulin, cerebral pro-glucagon, cerebral pro-glucagon-like peptide, cerebral pro-somatostatin, cerebral pro-pancreatic peptide, cerebral pro-GHRH, cerebral neuropeptide melamin-concentrating hormone, cerebral NEI, cerebral neurotensin, and cerebral opioid peptides, and then adding at least one spheron component peptide to the cell culture. Test compounds then can be added to the cell culture and the amounts of the respective cerebral components listed above can be measured. Useful test compounds are identified as those compounds used in the afore-mentioned example, whereby the cultures to which they were added had increased cerebral ACTH, cerebral insulin, cerebral enkephalins, cerebral TRH, cerebral dynorphin, cerebral αMSH and βendorphin, cerebral pro-insulin, cerebral pro-glucagon, cerebral pro-somatostatin, cerebral pro-pancreatic peptide, cerebral pro-GHRH, cerebral neuropeptide melamin-concentrating hormone, cerebral NEI, cerebral neurotensin, and cerebral opioid peptides, when compared to control cultures to which no test compounds were added.

The useful test compounds also will be those compounds that: (i) impede or prevent the release by a spheron of proSAAS or peptide fragments thereof; (ii) bind to, inhibit, antagonize, or compete with proSAAS or peptide fragments thereof that are released by a spheron; or (iii) reduce or prevent the cytotoxic effects of proSAAS or peptide fragments thereof that are released by a spheron. Those skilled in the art will be capable of utilizing the isolates spheron components described herein to assay for useful compounds, using the guidelines provided herein.

Various embodiments of the invention also relate to a method of identifying compounds useful in treating or ameliorating a neurological condition caused by spheron component peptides that includes culturing reproducible cells, and then transforming, transfecting, infecting, or otherwise inducing the cultured, reproducible cells to express proSAAS or a peptide fragment, variant, derivative, homologue, or mimetic thereof. The method then includes administering to the cultured cells a test compound, and then determining whether the test compound ameliorated, eliminated, or reduced the effects of the proSAAS or a peptide fragment, variant, derivative, homologue, or mimetic thereof, when compared to controls.

Another aspect of the present invention includes a composition comprising at least one compound capable of preventing or reducing the effects of spheron component peptides. The composition can include at least one isolated polypeptide or other compound that binds to, antagonizes or competes with a spheron component peptide other than a spheron component responsible for forming amyloid plaque. These isolated polypeptides or other compound can be identified using the testing protocol described briefly above, and in more detail below. Those skilled in the art are capable of manufacturing and isolating polypeptides or other compounds that bind to, antagonize, or compete with the above-described spheron component, using the guidelines provided herein.

This invention also includes polypeptides that are antibodies to spheron component peptides, proSAAS or its peptide fragments, racemized peptides and fragments, domains and subunits. Those skilled in the art are capable of generating polyclonal and monoclonal antibodies that bind to spheron component peptides, proSAAS or its peptide fragments, domains and subunits. Those skilled in the art are capable of using such antibodies to create antibody fragments, including short chain antibodies, and chimeric or humanized antibodies which have similar or better binding characteristics but have more favorable pharmacological properties such as reduced antigenicity, better bioavailability, easier manufacture and better blood-brain barrier penetration.

This invention also includes polypeptides that are subsequences or fragments of the protein receptors to which the spheron component peptides, proSAAS or its peptide fragments, racemized peptides, domains and subunits bind. The protein referred to include proprotein convertases such as PC1/3, PC2, PC4, PACE4, PC5/6, PC7 and furin. Such polypeptides would be selected on the basis of their ability to bind to spheron component peptides, proSAAS or its peptide fragments, domains and subunits and thereby compete with the protein substrate or receptor. This invention also includes variants, homologs, fusion proteins and peptide mimetics of such polypeptides and the modification of such polypeptides to increase the binding of the polypeptide to the spheron component peptides, proSAAS or its peptide fragments, domains and subunits by, for example, incorporating a chloromethylketone derivative such as lysyl or arginyl chloromethylketone. Additional compounds useful in this regard include proprotein convertase PC!, and active sites thereon selected from the group consisting of:

| ENKHG; | (SEQ ID NO. 24) |
| LDGIVTDAIE; | (SEQ ID NO. 25) |

-continued

| SWGPNDD; | (SEQ ID NO. 26) |
| WASGNG; | (SEQ ID NO. 27) |
| CDGYTDSIYTI; and | (SEQ ID NO. 28) |
| HTGTS. | (SEQ ID NO. 29) |

The composition also preferably includes at least one isolated polypeptide or compound that impedes or prevents the release from a spheron proSAAS or a peptide fragment thereof other than a spheron component responsible for forming amyloid plaque. These isolated polypeptides or compounds can be identified using the testing protocol described briefly above, and in more detail below. In addition, the compositions of the invention preferably include at least one isolated polypeptide or compound that reduces or prevents the cytotoxic or other deleterious effects of a spheron component peptide other than a spheron component responsible for forming amyloid plaque. These isolated polypeptides can be identified using the testing protocol described briefly above, and in more detail below.

The composition can be administered in a therapeutically effective amount to an animal in need thereof, e.g., an animal having at least one spheron component peptide in its neuronal grey matter in a cytotoxic amount. The method of administering the composition according to the invention includes, but is not limited to, administering the composition intramuscularly, orally, intravenously, intratumorally, intrathecally, intranasally, topically, transdermally, via an aerosol, etc.

Solid dosage forms for oral administration include capsules, tablets, pills, powders, and granules. In such solid dosage forms, the active compound is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alginates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as acetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Another method of administering the compositions of the invention is by a transdermal or transcutaneous route. One example of such an embodiment is the use of a patch. In particular, a patch can be prepared with a fine suspension of the composition in, for example, dimethylsulfoxide (DMSO), or a mixture of DMSO with cottonseed oil and brought into contact with the skin of the tumor carrying mammals away from the tumor location site inside a skin pouch. Other mediums or mixtures thereof with other solvents and solid supports would work equally as well. The patch can contain one or more of the test compounds described above in the form of a solution or a suspension. The patch can then be applied to the skin of the patient, for example, by means of inserting it into a skin pouch of the patient formed by folding and holding the skin together by means of stitches, clips or other holding devices. This pouch should be employed in such a manner so that continuous contact with the skin is assured without the interference of the mammal. Besides using a skin pouch, any device can be used which ensures the firm placement of the patch in contact with the skin. For instance, an adhesive bandage could be used to hold the patch in place on the skin.

Actual dosage levels of active ingredients in the compositions of the invention may be varied to obtain an amount of one or more test compounds that is effective to obtain a desired therapeutic response for a particular composition and method of administration. The selected dosage level therefore depends upon the desired therapeutic effect, the route of administration, the desired duration of treatment, the size of the animal being treated, and other factors.

With mammals, including humans, the effective amounts can be administered on the basis of body surface area. The interrelationship of dosages for animals of various sizes, species, and humans (based on mg/M$^2$ of body surface) is described by E. J. Freireich et al., *Cancer Chemother. Rep.*, 50(4):219 (1966). Body surface area may be approximately determined from the height and weight of an individual (see e.g., Scientific Tables, Geigy Pharmaceuticals, Ardsley, N.Y. pp. 537-538 (1970)).

The total daily dose of composition to a host may be in single or divided doses. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, potency of the administered drug, rates of absorption and excretion, combination with other drugs and the severity of the particular disease being treated.

Because the composition is targeted to prevent unwanted cytoxicity and other deleterious effects in the brain, the method of administration can encompass formulating a composition to further contain an agent that enables the test compound to cross the blood-brain barrier. Such methods of administration are described in, for example, U.S. Pat. Nos. 5,008,257, 4,824,850, 4,479,932, 4,727,079, 4,622,218, and 4,540,564 the disclosures of which are incorporated by reference herein in their entirety.

The treatment of nervous system disorders or other brain-related disorders can be achieved by administering drugs that affect nervous system function or dysfunction in animals or patients. Typically, such drugs are administered by peripheral application, either via the oral or the systemic route. While some drugs are able to cross the blood brain barrier (bbb), others do not pass the bbb efficiently or not at all and are only effective when given directly into the brain. The term "blood-brain barrier" or "bbb", as used herein, refers to the bbb proper as well as to the blood-spinal barrier. The blood-brain barrier, which consists of the endothelium of the brain vessels, the basal membrane and neuroglial cells, acts to limit penetration of substances into the brain. Sometimes the structure of the bbb is subdivided into two components: the endothelial or capillary barrier and the ependymal barrier. Banks, W. A., Kastin, A. J., Barrera, "Delivering peptides to the central nervous system: Dilemmas and strategies," *Pharm. Res.* 8:1345-1350 (1991).

The nature of the substance penetration through the bbb has not yet been determined but it is known that many of the regulators of brain function such as cytokines, transferrin, encephalins and endorphines can pass through the bbb from the blood vessels into the brain Raeissi, S., Audus, J., "In vitro characterization of blood-brain barrier permeability to delta sleep-inducing peptide." *J. Pharm. Phy.* 41:848-852(1989); Zlokovich, B., Susie, V. T., Davson, H. Begley, D. J., Jankov, R. M., Mitrivic, B. M., Lipovac, M. N., "Saturable mechanism for delta sleep-inducing peptide (DSIP) at the blood-brain barrier of the vascularly perfused guinea pig brain." *Peptides* 10:249-254(1989); and Zlokovich, B., "In vivo approaches for studying peptide interaction at the blood-brain barrier." *J. Control. Rel.* 13:185-201(1990). However, many substances that can affect the Central Nervous System (or CNS) such as adenosine, β-endorphin, synthetic analogs of endogenous peptides Houghten, R. A. Swann, R. W., Li, C. H., "β-Endorphin: Stability, clearance behaviour and entry into the central nervous system after intravenous injection of the tritiated peptide in rats and rabbits." *Proc. Natl. Acad. Sci. USA* 77:4588-4591(1980); Levin, E. R., Frank, H. J. K., Weber, M. A., Ismail, M., Mills M., "Studies on penetration of the blood-brain barrier by atrial natriuretic factor." *Biochem. Biophys. Res. Commun.* 147:1226-1231(1987) Sakane, T., Tanaka, C., Yamamoto, A., Hashida, M., Sesaki, H., Ueda, H., Takagi, H., "The effect of polysorbate 80 on brain uptake and analgesic effect of D-kyoto." *Int. J. Pharm.* 57:77-83(1989), as well as some excitatory and inhibitor amino acids and trophic factors, penetrate poorly or not at all through the bbb. At present, drugs with no bbb penetration or poor bbb penetration can only be given by direct CNS infusion or by implantation of controlled-release polymers. (See, e.g., U.S. Pat. No. 4,883,666, Sabel et al.).

One way to overcome some of the limitations of traditional drug therapy is to increase the relative amount of drug that passes the bbb. The belief is that if one can increase the amount of the drug crossing the bbb while reducing the peripheral dose of a given drug or diagnostic substance, the peripheral side effects of the drug are also less severe, while at the same time maintaining the desired effect in the brain. A number of approaches have been described as effective in increasing drug penetration through the bbb.

One approach has been to alter the function of the bbb itself. For instance, osmotic agents, when given peripherally (such as by intravenous injection), result in the opening of the bbb. Further, some drugs acting on the CNS can change the permeability of the bbb for other substances; cholinomimetic arecolines, for instance, have been reported to induce changes of drug penetration through the bbb Saija, A., Princi, P., De Pasquale, R., Costa, G., "Arecoline but not haloperidol produces changes in the permeability of the blood-brain barrier in the rat." *J. Pharm. Pha.* 42:135-138 (1990).

Other drugs that can be administered to alter the permeability of the bbb are disclosed in U.S. Pat. Nos. 5,059,415 and 5,124,146, both issued to E. A. Neuwelt. Bradykinin is one specific drug with such effects. (U.S. Pat. No. 5,112,596, issued to Malfroy-Camine). Another method comprises administering permeabilizer peptides such as A-7 or conformational analogs thereof. (WO 92/18529, an application of J.

W. Kozarich et al.). A relatively invasive method has been proposed by A. Tomasz and E. Tuomanen (WO 91/16064) who administer parenteral injections of purified cell wall or cell wall fragments of eubacteria such as *Streptococcus pneumoniae* to open the bbb.

U.S. Pat. No. 5,260,210 issued to L. L. Rubin et al., discloses a method whereby the permeability of the blood-brain barrier is increased by administering an agent that reduces or interferes with cyclic AMP concentrations or that increases cyclic GMP concentrations.

Another approach is the modification of the drug molecules themselves. For instance, macromolecules, such as proteins, do not pass the bbb at all, or pass through with difficulty or with alterations that adversely impact the proteins efficacy. For example, one can first isolate the macromolecule active site, i.e., the portion of the molecule that triggers the biologically desirable event, and then use only this active site. Since size is one of the factors in allowing permeability of the bbb, the reduced size can be used so that the smaller molecule can now pass the bbb. Other modifications to macromolecules to attempt passage of the bbb include glycating the proteins, thereby enhancing their permeability of the bbb, or forming a prodrug. U.S. Pat. No. 5,260,308, issued to J. F. Podusio and G. L. Curran, discusses glycating proteins, while U.S. Pat. No. 4,933,324 and WO 89/07938, both on applications of V. E. Shashoua, disclose formation of a prodrug. These prodrugs are formed from a fatty acid carrier and a neuroactive drug which is unable to pass across the bbb on its own. A similar system is disclosed in WO 89/07938.

Still another approach is the implantation of controlled release polymers that release the active ingredient from a matrix-system directly into the nervous tissue. However, this approach is invasive and requires surgical intervention if implanted directly into the brain or spinal cord (see Sabel et al. U.S. Pat. No. 4,883,666; and Sabel et al. U.S. patent application Ser. No. 07/407,930). It also is known to administer compositions directly to internal portions of the brain, as disclosed on U.S. Pat. No. 5,800,390, the disclosure of which is incorporated by reference herein in its entirety. These methods enable the delivery of sustained release, solid preparations and semi-solid preparations directly to brain tissue.

To overcome these limitations, another approach has been tried in which drug carrier systems are used such as liposomes, erythrocyte ghosts, antibody-conjugates, and monoclonal antibody conjugates. One of the major problems in targeted drug delivery is the rapid opsonization and uptake of injected carriers by the reticuloendothelial system (RES), especially by the macrophages in the liver and spleen. This obstacle may be partially overcome in the case of liposomes by incorporation of so-called "stealth" lipids, such as phosphatidylinositol, monosialoganglioside, or sulfogalactosylceramide.

U.S. Pat. Nos. 5,182,107 and 5,154,924, both issued to P. M. Friden, teach a method of conjugating a drug with an antibody where the antibody is reactive with a transferrin receptor. Transferrin receptors are located on brain capillary endothelial cells, which thus can transport a drug, such as nerve growth factor, across the bbb. U.S. Pat. No. 5,004,697 (issued to Pardridge) improves such an antibody-conjugate method by providing cationized antibodies with a specific isoelectric point (see also WO 89/01343 by Pardridge).

Another approach is to create chimeric peptides to which the active agents are conjugated (U.S. Pat. No. 4,801,575, also issued to Pardridge). Such a system is further discussed also in U.S. Pat. No. 4,902,505, issued to Pardridge and Schimmel, in which the chimeric peptide, such as histone, is capable of crossing the bbb by transcytosis.

U.S. Pat. Nos. 5,187,158 and 5,017,566, both issued to N. S. Bodor, disclose a brain-specific drug delivery method wherein a centrally acting drug is given with the reduced, biooxidizable lipoidal form of a dihydropyridine reaction-pyridine salt redox carrier such as dopamine. (See also U.S. Pat. No. 4,880,816, also issued to Bodor).

A rather invasive approach is taken to deliver genetic material to the brain. This is done, for example, by chemically disrupting the bbb and then using viruses to deliver genes across the bbb. (See, U.S. Pat. No. 4,866,042, issued to E. A. Neuwelt). Here, a corrective genetic material is incorporated into a virus and the virus is then injected into the bloodstream.

Finally, yet another carrier system to deliver drugs across the bbb is the use of liposomes, as disclosed by F. D. Collins and R. C. Thompson (WO 91/04014). Here, liposomes are targeted to specific endogenous brain transport systems that transport specific ligands across the bbb.

Another approach is disclosed in U.S. Pat. No. 6,117,454, to Kreuter, et al. The subject matter of the Kreuter patent includes a method, composition and drug targeting system using surfactant coated nanoparticles as a drug carrier (or targeting molecule) for a wide range of drugs in order to enhance the penetration of drugs or diagnostic agents across the bbb. Any of these methods can be used in the invention to administer a component, (e.g., compound, composition, peptide, gene, etc.) capable of preventing the cytotoxic effect of the spheron component peptides discussed above into the brain.

Another embodiment of the invention encompasses an Alzheimer's Disease symptom animal model, a method of making the animal model, and a method of using the animal model to identify effective therapies for treating or ameliorating brain damage or other disorders or maladies caused by spherons releasing component peptides other than those directly responsible for forming amyloid plaque. The animal model comprises an animal having a gene inserted into the brain thereof, whereby the gene expresses proSAAS, or one or more spheron component peptides selected from the group defined above, or variants, derivatives, homologues, peptide mimetics, or racemized peptides thereof. The method of making the animal model therefore includes preparing a gene that over-expresses proSAAS or one or more of spheron component peptides selected from the group defined above, incorporating the gene into the brain of an animal (e.g. by making a transgenic animal, using viral vectors to insert the gene into the central nervous system, or by other methods known in the art), and inducing the gene to over-express the proSAAS or spheron component peptide.

The method of using the animal model includes preparing a group of animals having a gene or genes in the brain thereof that over-expresses proSAAS or one or more of spheron component peptides selected from the group defined above, and then inducing the gene to over-express the proSAAS or spheron component peptide. The method further includes administering to a select group of animals a test compound, sacrificing the animals, and then measuring the amount of isolated spheron component peptides present in the sacrificed animal's brain, and/or measuring the percentage of viable cells at or around the locus of the gene and/or by measuring injury in relation to the protein expression, and/or measuring behavioral or other brain functional parameters. The method concludes by selecting those test compounds that reduce the amount of isolated spheron component peptides, when compared to controls, and/or by selecting those test compounds that yield a higher percentage of viable cells at or around the locus of the gene, when compared to controls having no test compound administered thereto, and/or by selecting those test compounds that reduce injury in relation to the protein expression, and/or by selecting those test compounds that improve brain function or behavior, etc. compared to controls.

The method of using the animal model to screen for effective test compounds also entails preparing the animal model as described above, and then inducing the gene to overexpress the proSAAS or one or more spheron component peptides selected from the group defined above, or variants, derivatives, homologues, or peptide mimetics thereof. The method further includes administering to a select group of animals a test compound, sacrificing the animals, and then measuring the amount of one or more of the following: (i) cerebral ACTH; (ii) cerebral insulin; (iii) cerebral enkephalins; (iv) cerebral TRH; (v) cerebral dynorphin; or (vi) any of the other components descrbed previously, such as glucagon, GLP, neurotensin, and the like. The method concludes by selecting those compounds that, when administered, reveal an increased level of any one of the five components, when compared to control animals to which no test compound were administered.

Introducing one or more copies of the proSAAS, or spheron component peptides into an animal first entails making a gene that expresses the respective peptide(s), or that can be induced to express the peptide(s) described above. The gene then can be introduced into the brain of the animal by transgenic animal techniques known in the art. The gene then will express the spheron component peptide(s), or can be induced to over-express the spheron component peptide(s). Using the guidelines provided herein, those skilled in the art are capable of making a gene that expresses one or more of the above-described peptides without undue experimentation. Means of gene delivery to a cell or tissue include direct injection of bare DNA, ballistic methods, use of a viral vector such as a retrovirus, adenovirus, adeno-associated virus, pox virus or herpes simplex virus, use of a DNA-protein conjugate and use of a liposome. Examples of using viral vectors to introduce genes into the central nervous system to treat brain disorders such as Parkinson's disease are disclosed in U.S. Pat. No. 6,248,320, the disclosure of which is incorporated by reference herein in its entirety.

The preferred spheron component peptides are those that are not directly involved in the formation of amyloid plaque, and more preferably are those listed above as SEQ ID NOS. 1-23, as well as their racemized analogs. However, the use of other spheron component peptides based on portions or fragments of other molecules of the same protein or protein family as the above-described spheron component peptides, also is encompassed by and included within the scope of the expression "spheron component peptide." Moreover, the invention includes other proteins that contain in whole or part any of the aforementioned spheron component peptides, whereby the proteins preferably possess the same, similar, or enhanced bioactivity as the spheron component peptide.

It will be apparent to one of skill in the art that other smaller fragments of the above peptides may be selected by one of skill in the art and that these peptides will possess the same or similar biological activity. Other fragments may be selected by one of skill in the art such that these peptides will possess the same or similar biological activity. The peptides of the invention encompass these other fragments, species, and proteins. In general, the peptides of this invention have at least 6 amino acids, preferably at least 5 amino acids, and more preferably at least 4 amino acids.

The invention also encompasses "combinations" of the peptides whereby two or more spheron component peptides are joined together, even if the sequences of the two peptides are not contiguous in the sequence of the specie(s) of spherons from which the spheron component peptides were derived. To the extent that a spheron component peptide has the desired biological activity, it follows that two such peptides would also possess the desired biological activity, even if these segments were not contiguous within the sequence of amino acids of the specie(s) of spherons from which the spheron component peptides were derived.

This invention also comprises reverse-D peptides based on the amino acid sequences of the spheron component peptides. The phrase "reverse-D peptide" refers to peptides containing D-amino acids, arranged in a reverse sequence relative to a peptide containing L-amino acids. Thus, the C-terminal residue of an L-amino acid peptide becomes the N-terminal for the D-amino acid peptide, and so forth. The invention further comprises racemized peptides whereby one or more of the amino acids residues (other than glycine) has: (i) been converted from an L stereoisomer to a D stereoisomer; (ii) been replaced by a D stereosiomer form; or (iii) otherwise undergone other stereoisomeric changes.

The invention also encompasses peptides that comprise spheron component peptides with additional amino acid residues before or after the spheron component peptide sequence on linker peptides. The additional amino acid residues or linker peptides may be those found in the spheron sequence before and after the spheron component peptide sequence, or they may comprise other amino acids or linker peptides. For example, a cysteine residue may be added at both the amino and carboxy terminals of the spheron component peptide in order to allow the cyclisation of the spheron component peptideby the formation of a di-sulphide bond.

The invention also encompasses fusion proteins where a spheron component peptide is fused with another protein, optionally linked by a peptide linker. Such a fusion protein can increase the bioactivity or bioavailability of the spheron component peptide in the body or the issue in which it is injected.

The invention also encompasses homologs and variants of spheron component fragments. It is common to vary peptide sequences by substituting one amino acid for another. Depending on the purpose for which the amino acid is being varied, the amino acid can be replaced with a similar or homologous amino acid or a dissimilar amino acid. There are many scales on which amino acids can be ranked as similar or homologous. (Gunnar von Heijne, *Sequence Analysis in Molecular Biology*, p. 123-39 (Academic Press, New York, N.Y. 1987).

Spheron component peptides and homologs, variants, derivatives, combinations, racemized peptides, and salts thereof can be made using conventional peptide synthesis techniques known to one of ordinary skill in the art. These techniques include chemical coupling methods (cf. Wunsch, E: "Methoden der organischen Chemie", Volume 15, Band 1+2, *Synthese von Peptiden, thime Verlag, Stuttgart* (1974), and Barrany, G.; Marrifield, R. B.: "The Peptides", eds. E. Gross, J. Meienhofer, Volume 2, Chapter 1, pp. 1-284, Academic Press (1980)), enzymatic coupling methods (cf. Widmer, F. Johansen, J. T., *Carlsberg Res. Commun.*, Vol. 44, pp. 37-46 (1979), and Kullmann, W.: "Enzymatic Peptide Synthesis" CRC Press Inc. Boca Raton, Fla. (1987), and Widmer, F., Johansen, J. T. in "Synthetic Peptides in Biology and Medicines:, eds. Alitalo, K., Partanen, P., Vatieri, A., pp. 79-86, Elsevier, Amsterdam (1985)), or a combination of chemical and enzymatic methods if this is advantageous for the process design and economy. Those skilled in the art are capable of varying the peptide sequence of the spheron component peptides to make a homolog having the same or similar biological activity (bioactivity) as the original or native spheron component peptide, using the guidelines provided herein.

The invention also encompasses peptide mimetics and racemized peptides based on spheron component peptides and structural modifications of spheron component peptides where the resulting compound retains the chemical reactivity and hence the same biological activity as the spheron component peptides. Peptide mimetics are compounds that mimic the biological activity of a peptide but are no longer peptidic in chemical nature, that is, they no longer contain any peptide bonds (that is, amide bonds between amino acids). Here the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to this invention provide a spatial arrangement of reactive chemical moieties that closely resemble the three-dimensional arrangement of active groups in the spheron component peptide on which the peptide mimetic is based. As a result of this similar active-site geometry, the peptide mimetic has effects on biological systems that are similar to the biological activity of the peptide.

The invention also includes various cell lines that have been transfected, transformed, or infected in accordance with the methods of the invention. These cell lines preferably include recombinant cells that express a nucleic acid sequence that encodes proSAAS, or a peptide fragment, racemized peptide, variant, derivative, homologue, or mimetic thereof. It is most preferred that the cell lines include recombinant cells that express a nucleic acid sequence that encodes an amino acid sequence selected from SEQ ID NOS. 1-14, or combinations thereof.

The invention also encompasses a protein that includes one or more spheron component peptides selected from the group:

```
                          (SEQ ID NO. 1)
GEAAGAVQELAR;

(SEQ ID NO. 2)
GLSAASPPLAETGAPR;

(SEQ ID NO. 3)
ARAEAQEAEDQQAR;

(SEQ ID NO. 4)
VLAQLLR;

(SEQ ID NO. 5)
ALAHLLEAERQER;

(SEQ ID NO. 6)
AADHDVGSELPPEGVLGALLR;

(SEQ ID NO. 7)
LETPAPQVPAR;

(SEQ ID NO. 8)
ILAGSADSEGVAAPR;

(SEQ ID NO. 9)
ARPVKEPRGLSAASPPLAETGAPRRF;
```

```
                          -continued
                          (SEQ ID NO. 10)
ARPVKEP;

(SEQ ID NO. 11)
GLSAASPPLAETGAPRRF;

(SEQ ID NO. 12)
AADHDVGSELPPEGVLGALLRVKRLETPAPQVPA;

(SEQ ID NO. 13)
AADHDVGSELPPEGVLGALLRV;

(SEQ ID NO. 14)
LETPAPQVPA;

(SEQ ID NO. 15)
RRSVPRGEAAG;

(SEQ ID NO. 16)
VLAQLLRVWGAPRNSD;

(SEQ ID NO. 17)
PALGLDDDPDAPAAQLAR;

(SEQ ID NO. 18)
LARALLRARLDPAALAA;

(SEQ ID NO. 19)
QLVPAPVPAAALRPRPPVYDD;

(SEQ ID NO. 20)
GPAGPDAEEAGDE;

(SEQ ID NO. 21)
TPDVDPELLRYLLGR;

(SEQ ID NO. 22)
LLRVKR; and (SEQ ID NO. 23)
VLGALLRVKRLE
``` wherein the spheron component peptide has been racemized. Preferably, at least one of the amino acid residues (other than glycine) of the spheron component peptide has: (i) been converted from an L stereoisomer form to a D stereoisomer form; (ii) been replaced by a D stereoisomer form; or (iii) otherwise undergone other steeoisomeric changes.

The invention preferably includes a composition comprising the protein described in the paragraph above, and more preferably, a protein compsiring one or more peptides selected from SEQ ID NO. 1-SEQ ID NO. 8. It is even more preferred in the invention that the protein is a prSAAS or a fragment, variant, derivative, homologue, peptide mimetic thereof, and where where at least one of the amino acid residues (other than glycine) in the peptides listed above has been converted from an L stereoisomer form to a D stereoisomer form, has been replaced by a D stereoisomer form, or has otherwise undergon other stereoisomeric changes.

The following examples are provided to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLES

Example 1

Spherons were extracted and purified to homogeneity from human brain according to the method of U.S. Pat. Nos. 6,309, 892, and 5,525,339. Samples of homogeneous spherons were separated by polyacrylamide gel electrophoresis according to standard methods recited in U.S. Pat. Nos. 6,309,892, and 5,525,339. The bands on the gels were transferred to nitrocellulose blots by standard methods well known in the art. These bands were further analyzed by high performance liquid chromatography and amino acid microsequencing analysis.

The following sequences were among those detected from purified homogeneous dense microsphere preparations:

```
1)   GEAAGAVQELAR;             (SEQ ID NO. 1)
2)   GLSAASPPLAETGAPR;         (SEQ ID NO. 2)
3)   ARAEAQEAEDQQAR;           (SEQ ID NO. 3)
4)   VLAQLLR;                  (SEQ ID NO. 4)
5)   ALAHLLEAERQER;            (SEQ ID NO. 5)
6)   AADHDVGSELPPEGVLGALLR;    (SEQ ID NO. 6)
7)   LETPAPQVPAR;              (SEQ ID NO. 7)
8)   ILAGSADSEGVAAPR;          (SEQ ID NO. 8)
```

These sequences are consistent with all or a portion of a protein referred to as pro-SAAS, and also known as granin-like neuroendocrine peptide precursor.

Example 2

Polypeptides corresponding to spheron component peptides sequenced in Example 1 were synthesized and tested in neuronal cell cultures. The spheron component peptides in phosphate buffered saline (PBS) were incubated alone and in combination into glioma cell cultures and neuroblastoma cell cultures. Controls of
1) homogeneous samples of spherons, 0.1-10 mg protein/mL;
2) phosphate buffered normal saline alone;
3) tamoxifen, 100 µM;
4) DMSO; and
5) bovine serum albumin, 5 mg/mL.

also were tested in the cultures.

Cell Culture:

Cryopreserved glioma and neuroblastoma cells were acquired from the American Type Culture Collection (ATCC), Virginia. Cells were thawed and diluted in suspension media and centrifuged at 700 rpm for 7 minutes at 4 C. Cell pellets then were resuspended in CACO-2 media and cultured in standard 75 or 175 $cm^2$ flasks at 37 C., 5% CO(2) until approximately confluent. The cells were then trypsinized and resuspended in CACO-2 media to achieve a final cell density of $1.5 \times 10^5$ cells/mL. 50 µL aliquots per sample were then added per well to 96 well plates.

Dosing:

For Experiment I, 50 µL of either PBS (phosphate buffered solution) (negative control), 100 µM tamoxifen in phosphate buffered saline PBS (positive control), or test article were added to each sample culture.

For Experiment II, 1 mM tamoxifen in DMSO (dimethylsufoxide) was diluted to 100 µM concentration in CACO-2 media, and 100 µL per well was added to positive control wells. A vehicle control consisting of 1% DMSO in CACO-2 media was also added to this experiment. Other negative controls consisted of human and bovine serum albumin.

MTT Assays:

An MTT assay is a sensitive assay for the measurement of cell proliferation based upon the reduction of the tetrazolium salt 3, [4,5-dimetylthiazol-2-yl]-2,5-diphenyltetrazolium bromide (MTT). Following incubations with control or test substances, media was aspirated and 100 µL MTT was added to each well. Plates were then incubated for 3 hours at 37 C., 5% CO(2). MTT was then replaced with acidified isopropanol (0.4 N HCl) and the plates were stored overnight at 4 C., covered. Plates were then agitated gently for 1 minute on a rotary shaker and the difference between emission absorbance of 570 nm and background absorbance of 650 nm was measured spectrophotometrically on an automated plate reader.

Results:

Experiment I:

Glioma cells were incubated for 24 hours and 96 hours following treatment with test materials or control solutions. MTT was added to all cultures at this time. Results are expressed as mean absorbance differences and represented as per cent of negative control and are shown in Table 3 and Table 4 (cytotoxicity in glioma cells).

TABLE 3

Cytotoxicity in glioma cells: 24 hrs.

| Test Article Identification | Concentration | ABS 570-690 Sample | SD | Percent of Viable Cells |
|---|---|---|---|---|
| NC (PBS) | | 0.093 | 0.016 | 100 |
| VC (DMSO) | | 0.079 | 0.004 | 100 |
| PC (Tamoxifen) | 100 µM | 0.014 | 0.004 | 18 |
| Synthetic peptide | 5 mg/mL | 0.044 | 0.020 | 72 |
| Spherons | 100-1000 ng/mL | 0.048 | 0.005 | 79 |

Abbreviations:
ABS, Absorbance;
NC, Negative Control;
PC, Positive Control;
SD, Standard Deviation;
VC, Vehicle Control.

TABLE 4

Cytotoxicity in glioma cells: 4 days

| Test Article Identification | Concentration | ABS 570-690 Sample | SD | Percent of Viable Cells |
|---|---|---|---|---|
| NC (PBS) | | 0.590 | 0.048 | 100 |
| PC (Tamoxifen) | 100 µM | 0.700 | 0.052 | 63 |
| Synthetic peptides i | 5 mg/mL | 0.150 | 0.032 | 25-75 |
| Synthetic peptides ii | 5 mg/mL | 0.030 | 0.003 | 5-50 |
| Spherons | | 0.070 | 0.014 | 11-60 |

Abbreviations:
ABS, Absorbance;
NC, Negative Control;
PC, Positive Control;
SD, Standard Deviation;
VC, Vehicle Control Experiment II:

Neuroblastoma cells were used for this experiment. MTT was added to the plates following a 24 hour and 96 hour incubation with control or test solutions. Other plates were replenished with fresh media, control, or test solution at 24 hours and then read 3 days later. Results are expressed as mean absorbance differences and as per cent of negative control and are shown in Table 5. Similar results were found in 96 hours.

TABLE 5

Neuroblastoma cells: 24 hour incubation

| Test Article Identification | Concentration | ABS 570-690 Sample | SD | Percent of Viable Cells |
|---|---|---|---|---|
| NC (PBS) | | 0.089 | 0.009 | 100 |
| VC (DMSO) | | 0.073 | 0.004 | 100 |
| PC (Tamoxifen) | 100 μM | 0.010 | 0.001 | 14 |
| Synthetic proteins | 5 mg/mL | 0.012 | 0.003 | 13-60 |
| Synthetic proteins | 0.5 mg/mL | 0.050 | 0.011 | 52-70 |
| Synthetic proteins | 0.05 mg/mL | 0.057 | 0.004 | 59-70 |
| Spherons | | 0.059 | 0.037 | 61 |

Abbreviations:
ABS, Absorbance;
NC, Negative Control;
PC, Positive Control;
SD, Standard Deviation;
VC, Vehicle Control Conclusion:

Significant cytotoxic effects on glioma and neuroblastoma cells are apparent at 24 hours and in glioma cells at 96 hours with spherons and with synthetic spheron component peptides proteins from spherons.

Example 3

The synthetic peptides of Example 2, diluted in phosphate buffered saline at 1-5 mg/mL were inoculated into the cerebral cortex of 12 normal rats. Control rats received phosphate buffered saline. The animals were observed and painlessly sacrificed after intervals of 1, 4, and 10 days. The rat brains were fixed in 10% formalin, embedded in paraffin, sectioned and stained with hematoxylin-eosin and examined by light microscopy. In all examples, acute inflammatory reactions with extreme microglial reaction were observed. This degree of gliosis and inflammation was not found in the controls.

Example 4

The genes for spherons and genes for spheron component peptide fragments thereof are transfected into neuronal cell lines and expression of the genes is promoted. The neuronal cells are examined for evidence of abnormal cell loss and abnormal pathological changes.

Example 5

The genes for spherons and genes for spheron component peptide fragments thereof are transfected into experimental animal brains and expression of the genes is promoted. The experimental animals are observed for abnormal behavior, and the experimental animal brains are examined for evidence of histopathological abnormalities.

It will be apparent to those skilled in the art that various modifications and variations can be made in the methods and compositions of the present invention without departing from the spirit or scope of the invention. Thus, it is intended that the present invention cover the modifications and variations of this invention.

What is claimed is:

1. An isolated spheron component peptide consisting of the amino acid sequence of GEAAGAVQELAR (SEQ ID NO: 1) and up to 25 additional amino acids, wherein the spheron component peptide is cytotoxic.

2. The spheron component peptide of claim 1, wherein at least one of the amino acid residues of the spheron component peptide is aspartic acid or serine and wherein at least one of the aspartic acid or serine has been racemized from an L stereoisomer form to a D stereoisomer form.

3. The spheron component peptide of claim 1, wherein at least one peptide bond is substituted with a non-peptide bond.

4. The spheron component peptide of claim 1, wherein all of the peptide bonds have been substituted with non-peptide bonds.

5. A pharmaceutical composition comprising the spheron component peptide of claim 1 and a carrier thereof.

6. A pharmaceutical composition comprising the spheron component peptide of claim 3 and a carrier thereof.

7. A pharmaceutical composition comprising the spheron component peptide of claim 4 and a carrier thereof.

8. A spheron component peptide mimetic consisting of the amino acid sequence of GEAAGAVQELAR (SEQ ID NO:1) and up to 25 additional amino acids, wherein at least one peptide bond is substituted with a non-peptide bond, and wherein the spheron component peptide mimetic is cytotoxic.

9. The mimetic of claim 8, wherein at least one of the amino acid residues of the mimetic is aspartic acid or serine and wherein at least one of the aspartic acid or serine has been racemized from an L stereoisomer form to a D stereoisomer form.

10. The mimetic of claim 8, wherein all of the peptide bonds have been substituted with a non-peptide bonds.

11. A pharmaceutical composition comprising the spheron component peptide mimetic of claim 8 and a carrier thereof.

12. A pharmaceutical composition comprising the spheron component peptide mimetic of claim 9 and a carrier thereof.

* * * * *